United States Patent
Stobie

(10) Patent No.: US 8,202,314 B2
(45) Date of Patent: Jun. 19, 2012

(54) HOLDERS FOR PROSTHETIC AORTIC HEART VALVES

(75) Inventor: Robert Stobie, Errol (GB)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 12/856,341

(22) Filed: Aug. 13, 2010

(65) Prior Publication Data
US 2010/0312334 A1    Dec. 9, 2010

Related U.S. Application Data

(62) Division of application No. 11/405,819, filed on Apr. 14, 2006, now Pat. No. 7,806,926.

(51) Int. Cl.
*A61F 2/24* (2006.01)
(52) U.S. Cl. ...................................... 623/2.11
(58) Field of Classification Search .................. 623/2.11, 623/2.1
See application file for complete search history.

(56) References Cited

U.S. PATENT DOCUMENTS

| | | | |
|---|---|---|---|
| 4,106,129 A | 8/1978 | Carpentier et al. | |
| 4,585,453 A | 4/1986 | Martin et al. | |
| 5,037,434 A | 8/1991 | Lane | |
| 5,041,130 A | 8/1991 | Cosgrove et al. | |
| 5,197,979 A * | 3/1993 | Quintero et al. ............ | 623/1.26 |
| 5,290,300 A | 3/1994 | Cosgrove et al. | |
| 5,350,420 A | 9/1994 | Cosgrove et al. | |
| 5,476,510 A | 12/1995 | Eberhardt et al. | |
| 5,496,336 A | 3/1996 | Cosgrove et al. | |
| 5,683,402 A | 11/1997 | Cosgrove et al. | |
| 5,716,401 A | 2/1998 | Eberhardt et al. | |
| 5,800,531 A | 9/1998 | Cosgrove et al. | |

(Continued)

FOREIGN PATENT DOCUMENTS

WO    WO9725004    7/1997

(Continued)

OTHER PUBLICATIONS

Edwards Lifesciences, "Introducing the New Carpentier-Edwards Perimount Magna Aortic Valve Holder," 2005, 2 pages.

(Continued)

*Primary Examiner* — Melanie Tyson
*Assistant Examiner* — Son Dang
(74) *Attorney, Agent, or Firm* — AnneMarie Kaiser; Guy Cumberbatch

(57) ABSTRACT

A holder for a flexible leaflet prosthetic aortic heart valve that is less bulky than earlier holders and minimizes obstructions to vision and working space around the valve to facilitate implantation thereof. The holder may have a central hub and three outwardly extending legs that connect directly and exclusively to tips of the commissures of the aortic heart valve for better tactile feedback when parachuting and seating the valve in the annulus. The legs are sized so that they do not overlap the commissure tips and therefore afford a better view of the sewing ring adjacent the commissures. The legs may be narrow in the midsection or split into two rails to increase visibility of the valve leaflets. The hub may be vaulted axially upward relative to the outer ends of the legs to further increase visibility of the valve. A more secure engagement between the central hub and a delivery handle is also provided to ensure the holder/handle connection does not become loose during suture placement through the sewing ring and fewer handle revolutions are required to screw in and unscrew the handle from the holder.

27 Claims, 4 Drawing Sheets

U.S. PATENT DOCUMENTS

| | | | |
|---|---|---|---|
| 5,861,028 A | 1/1999 | Angell | |
| 6,019,790 A * | 2/2000 | Holmberg et al. | 623/2.11 |
| 6,283,993 B1 | 9/2001 | Cosgrove et al. | |
| 6,338,740 B1 | 1/2002 | Carpentier | |
| 6,558,416 B2 | 5/2003 | Cosgrove et al. | |
| 6,702,852 B2 | 3/2004 | Stobie et al. | |
| 6,736,845 B2 | 5/2004 | Marquez et al. | |
| 6,802,860 B2 | 10/2004 | Cosgrove et al. | |
| 6,964,682 B2 | 11/2005 | Nguyen-Thien-Nhon et al. | |
| 6,966,925 B2 | 11/2005 | Stobie | |
| 7,018,407 B1 | 3/2006 | Wright et al. | |
| 7,033,390 B2 | 4/2006 | Johnson et al. | |
| 7,189,258 B2 | 3/2007 | Johnson et al. | |
| 7,468,073 B2 | 12/2008 | Johnson et al. | |
| 7,503,929 B2 | 3/2009 | Johnson et al. | |
| 2002/0055775 A1 * | 5/2002 | Carpentier et al. | 623/2.17 |
| 2003/0125805 A1 * | 7/2003 | Johnson et al. | 623/2.11 |
| 2004/0059413 A1 | 3/2004 | Argento | |
| 2004/0148017 A1 * | 7/2004 | Stobie | 623/2.11 |
| 2006/0195181 A1 * | 8/2006 | Johnson et al. | 623/2.11 |
| 2006/0241743 A1 * | 10/2006 | Bergin et al. | 623/2.11 |
| 2008/0249620 A1 * | 10/2008 | Bicer | 623/2.11 |

FOREIGN PATENT DOCUMENTS

| | | |
|---|---|---|
| WO | WO0042950 | 7/2000 |
| WO | WO2004026173 | 4/2004 |

OTHER PUBLICATIONS

Edwards Lifesciences engineering drawing of a holder for a heart valve termed "PERI," short for "PERIMOUNT," Sep. 15, 1995.

Medtronic, "Advanced Implant System," 2003, 2 pages.

Medtronic, "The Cinch Advanced Implant System, Tehnology Made Easy," 2003, 2 pages.

Sorin Group Canada, Inc., Mitroflow Division, "Aortic Pericardial Heart Valve, Instructions for Use," 2004, 2 pages.

St. Jude Medical, "Experience Ease of Implant With Just One Touch," 2005, 4 pages.

St. Jude Medical, "Physician's Manual, SJM Biocor Valve," Aug. 6, 2005, 5 pages.

* cited by examiner

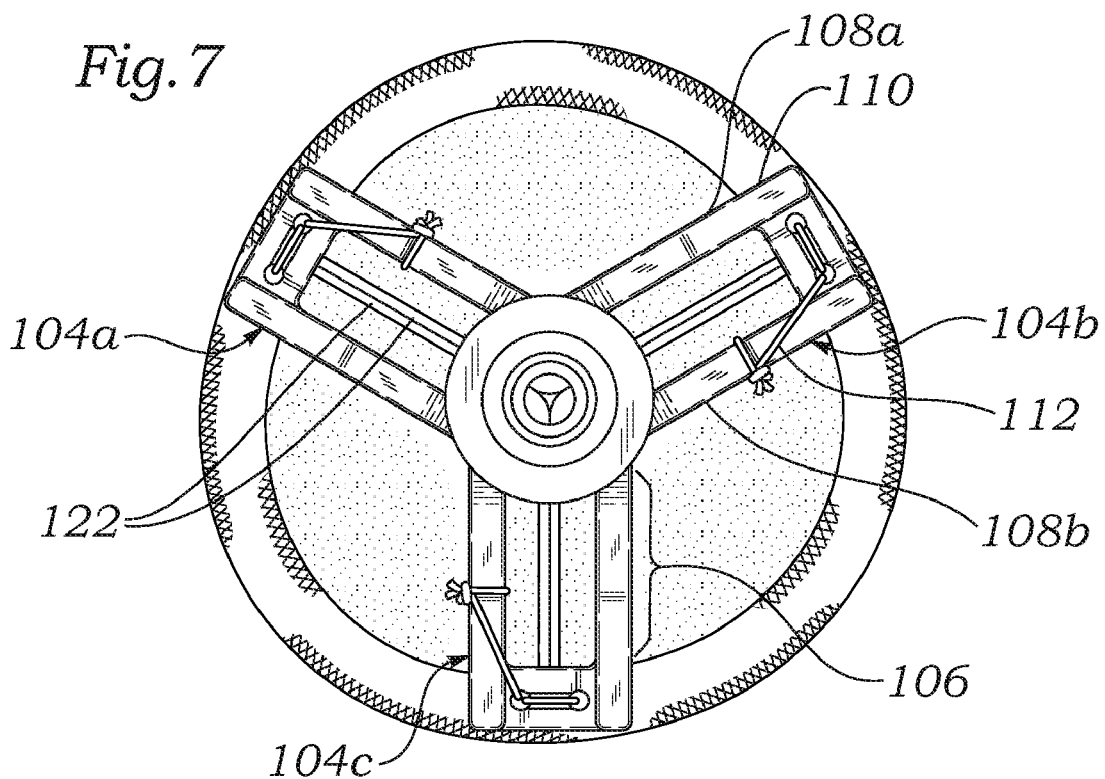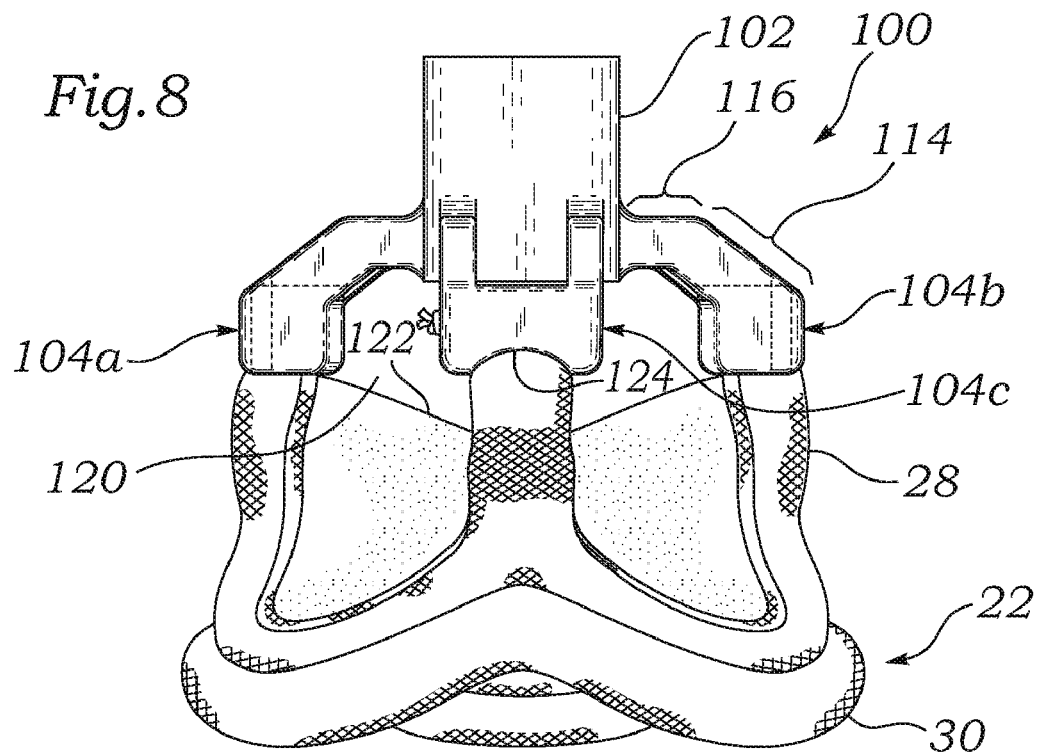

HOLDERS FOR PROSTHETIC AORTIC HEART VALVES

RELATED APPLICATIONS

The present application is a divisional of U.S. application Ser. No. 11/405,819, filed Apr. 14, 2006, now U.S. Pat. No. 7,806,926.

FIELD OF THE INVENTION

The present invention relates generally to medical devices, and more particularly to a holder that facilitates the implantation of a flexible leaflet prosthetic aortic heart valve, and associated methodology.

BACKGROUND OF THE INVENTION

In mammalian animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves, and each has leaflets to control the directional flow of blood through the heart. The valves are each supported by an annulus that comprises a dense fibrous ring attached either directly or indirectly to the atrial or ventricular muscle fibers. Various surgical techniques may be used to repair a diseased or damaged valve. In a valve replacement operation, the damaged leaflets are often excised and the annulus sculpted to receive a replacement valve. Sometimes the leaflets are heavily calcified and are left in place. Various types and configurations of prosthetic heart valves for replacing diseased natural human heart valves are known.

Two primary types of heart valve replacements or prostheses which include valve leaflets are those which have one or more relatively rigid leaflets formed of a stiff biocompatible material, and those which have flexible leaflets, typically made of a biological material. In the latter bioprosthetic or tissue valves, a whole xenograft valve (e.g., porcine) or a plurality of xenograft leaflets (e.g., bovine pericardium) provide occluding surfaces. Research is ongoing on synthesizing the tissue leaflets, and therefore the term "flexible leaflet valve" refers to both natural and artificial valves. Flexible leaflet valves may have a semi-rigid or relatively flexible frame or stent with (typically) three leaflets attached thereto, while some have no stent (stentless). In the former, the stent typically defines commissure posts projecting in an outflow direction that provide support between adjacent leaflets, and a substantially circular base surrounded by an annular or scalloped sewing ring for suturing the valve to surrounding tissue.

Examples of bioprosthetic valves are described in U.S. Pat. No. 4,106,129 to Carpentier et al., entitled "Supported Bioprosthetic Heart Valve with Compliant Orifice Ring," and in U.S. Pat. No. 5,037,434 to Lane, entitled "Bioprosthetic Heart Valve with Elastic Commissures." The Carpentier et al. '129 patent describes a stent comprising a single flexible wire preformed to define a generally circular base that is interrupted at circumferentially-spaced points by three inverted U-shaped commissure posts that project generally normally in the outflow direction with respect to the circular base. The Lane '434 patent describes a stent composed of a flexible metal ribbon similarly preformed to define three commissure posts that project generally normally with respect to a generally circular base. Both the Lane '434 and Carpentier et al. '129 patents describe a conventional configuration of three leaflets, wherein one leaflet is disposed between each pair of commissure posts.

To facilitate the implantation of heart valve prostheses, various types of specialized holders have been developed. Aortic valve holders are designed to enable the implanting surgeon to precisely position the heart valve and sewing ring either within the heart passageway or adjacent/above the aortic root of the patient and to securely hold the valve assembly in place until suturing is complete and the sutures are tied off.

Due to the usual approach through the aortic arch to the aortic annulus, holders for aortic valves are attached to the outflow end of the valve; i.e., the end having the commissure tips, and the valve advances with its inflow end leading. An elongate handle connects to the holder and is grasped and manipulated by the surgeon to maneuver the valve to its desired implantation position. The handle is then removed and the sewing ring sutured to the native valve annulus with the holder remaining attached to protect the valve. Certain shortcomings are associated with conventional aortic valve holders, including the presence of the holder that sometimes gets in the way out of the suturing operation. The holder as well as the upwardly projecting commissure posts can obstruct the surgeon's access to the valve base, making suturing of the sewing ring to surrounding tissue and tying-off of the implanting sutures difficult. Bulky holders may actually increase the potential for puncture of one of the leaflets or improper suturing.

Often, a so-called "parachute" method is employed wherein a circular array of sutures is first secured to the annulus and then passed in the same distribution through the sewing ring while it is still outside the body. The valve is then lowered into place along the circular array of sutures. Once the sewing ring is properly positioned against the annulus, the handle is removed so that the surgeon can more easily tie off the sutures on the visible (outflow) side of the sewing ring. As mentioned, the holder remains to protect the valve during suture tie-down and to ensure valve shape. Even with such an elaborate procedure, there is precious little space between the upstanding commissures and leaflets of the valve and the surrounding aortic wall for the surgeon to manipulate forceps to tie off the sutures. This is particularly evident in patients having a relatively small aortic root, and is exacerbated by bulky holders.

Some attempts at mitigating the sometimes obtrusive nature of aortic valve holders have been made. For example, U.S. Pat. No. 5,716,401 to Eberhardt, et al. discloses a holder for an aortic valve having a plurality of distally-projecting fingers adapted to engage the commissure posts of the valve. The fingers displace the commissure posts radially inward, and a mechanism is provided for retaining the fingers in that inward position, thus reducing obstacles to the surgeon's suturing operation. The Eberhardt holder is relatively complicated, however, and adds cost to the valve.

What is needed then is an elegant prosthetic aortic valve holder attachable to the outflow end of the valve that enhances visibility and facilitates implantation without the need for moving parts and the like.

SUMMARY OF THE INVENTION

The present invention provides an aortic valve holder for flexible leaflet valves that is significantly reduced in shape so as to facilitate valve implantation. The holder of the present invention is less bulky than earlier holders and minimizes obstructions to vision and working space around the valve to facilitate implantation thereof. The holder desirably connects directly and exclusively to tips of the commissures of the aortic heart valve for better tactile feedback during delivery. The legs are sized so that they do not overlap the commissure tips and therefore provide more space between the commissures and the wall of the aortic root to facilitate suture tie-down. The holder has no moving parts to minimize costs and may be molded into a variety of elegant shapes.

In accordance with one aspect of the invention, a prosthetic aortic heart valve and holder combination is substantially more rigid than before. The prosthetic aortic heart valve has an inflow end and an outflow end, the outflow end being defined by a plurality of generally axially extending commissure posts terminating in commissure tips. The holder has a central hub and a plurality of legs radially outwardly projected from the hub such that an outer end of each of the legs is located in proximity with one of the commissure tips. At least one attachment member connects each of the legs exclusively and directly to a corresponding tip of one of the commissure posts, extending from the holder just to the commissure tip. Desirably, the attachment members are sutures and each holder leg includes a cavity over which the corresponding attachment suture passes to enable the suture to be easily severed using a sharp.

In a preferred embodiment, the prosthetic aortic heart valve has flexible leaflets. Further, the prosthetic aortic heart valve is constructed with a fabric-covered inner stent member that extends up the commissure posts to the commissure tips. The holder legs project radially outward to contact the commissure tips at the radial location of the inner stent member but not as far as the outer radial extent of the commissure posts so as to provide greater space around the commissure posts and minimize obstructing the view of the inflow end of the valve during implantation. The commissure tips are fabric-covered and have a rounded configuration, and an inflow side of the outer ends of each of the holder legs has a concave configuration to match the rounded commissure tips.

Preferably, the outer end of each of the legs has valve attachment structure and a first width as seen in axial plan view. Each of the legs further includes a mid-section extending between the central hub and the outer end that has a total material width as seen in axial plan view that is less than 50% (preferably less than 33%) of the first width for enhanced visibility of the valve. In one embodiment, each of the legs has a single member mid-section narrower than the outer ends. In another embodiment, each of the legs has a mid-section that is split into two slim rails that are joined together at the outer end, wherein a radial gap is formed between the rails enabling direct axial viewing of the heart valve leaflet free edges therethrough. Each of the legs may have an axial component so as to vault the central hub away from the heart valve.

The present invention also provides a prosthetic heart valve holder comprising a central hub defining a central axis and a plurality of elongated legs projecting outwardly from an inflow end of the hub. Each of the legs terminates at an outer end having valve attachment structure and a first width as seen in axial plan view. An elongated mid-section extending between the central hub and the outer end of each leg has a total material width as seen in axial plan view that is less than 50% of the first width for enhanced visibility of a valve secured to the holder.

In one embodiment, the mid-section of each of the legs is split into two slim rails that are joined together at the outer end, wherein a radial gap is formed between the rails enabling direct axial viewing of a heart valve attached to the holder. Desirably, the two slim rails have a total material width as seen in axial plan view that is less than 50% (preferably less than 33%) of the first width. Alternatively, each of the legs has a single member mid-section narrower than the outer ends.

In a preferred embodiment, each of the legs has an axial component so as to vault the central hub axially from the outer ends of the legs. For example, each of the legs has an axially and radially angled segment and a purely radial segment. Desirably, an inflow side of the outer ends of each of the holder legs has a concave configuration to better mate with the tips of commissure posts of a prosthetic heart.

A more secure engagement between the central hub and a delivery handle is also provided to ensure the holder/handle connection does not become loose during suture placement through the sewing ring. Preferably, fewer handle revolutions are required to screw in and unscrew the handle from the holder.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIGS. 7 and 8 are top plan and front elevational views, respectively, of an exemplary holder of the present invention having a "vaulted split rail" configuration attached to a flexible leaflet aortic valve.

DETAILED DESCRIPTION OF THE PREFERRED EMBODIMENTS

The present invention provides an improved holder for prosthetic aortic heart valves, in particular flexible leaflet valves. It should be understood, however, that certain features of the holder of the present invention are equally applicable to delivering prosthetic aortic heart valves that have rigid leaflets. Namely, the holders of the present invention attach only to the commissure tips of the valve and provide enhanced visibility of the leaflets and outer extent of the valve, especially the peripheral sewing ring on the inflow end. Such an advantage may also be desirable when implanting mechanical valves.

Figure 1:
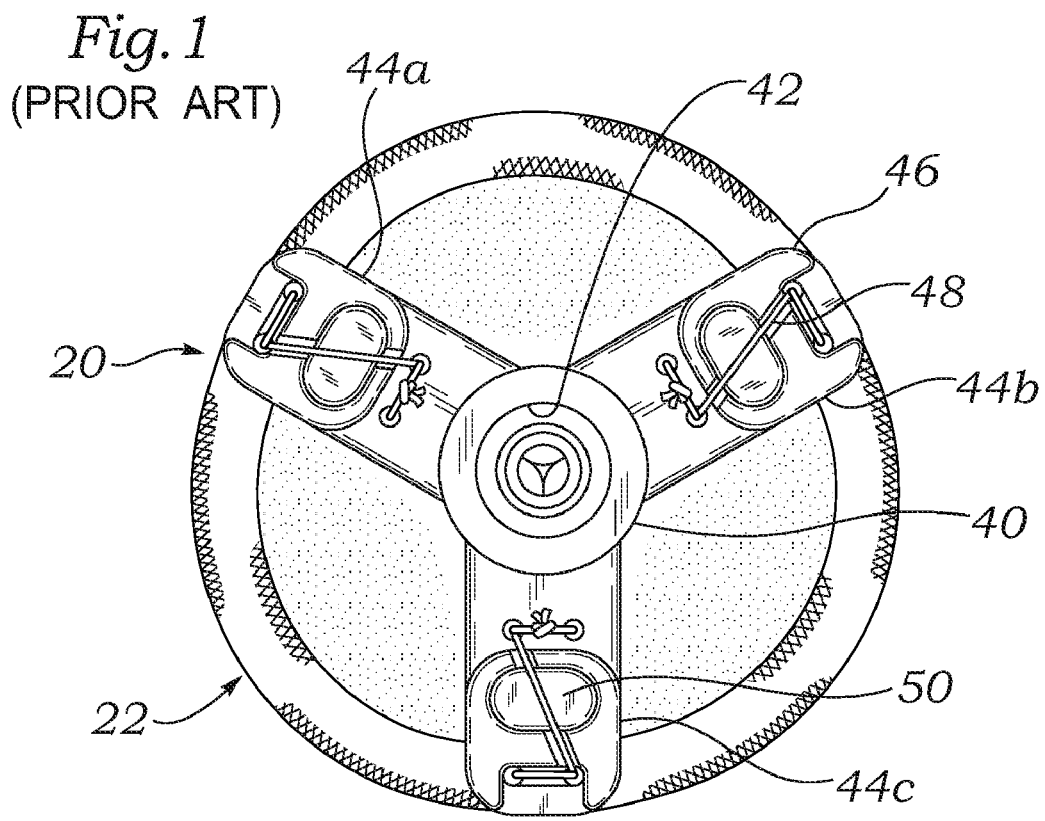
FIGS. 1 and 2 are top plan and front elevational views, respectively, of a prior art holder attached to a flexible leaflet aortic valve.
Figure 2:
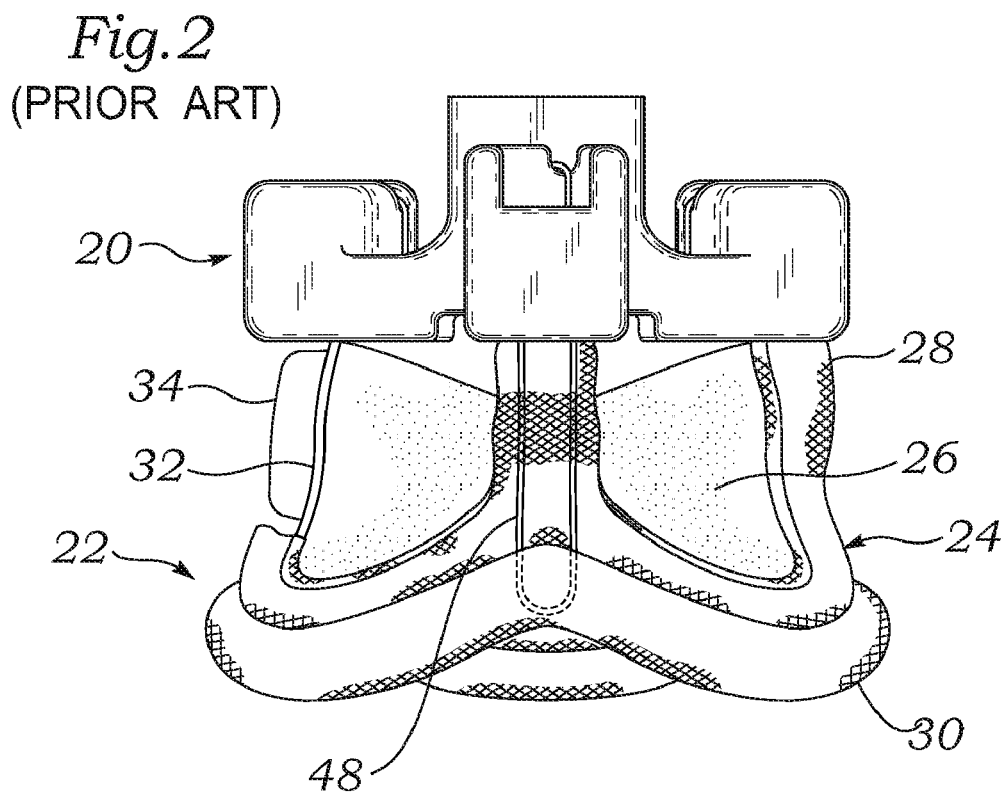

Is important to review modifications made to an existing aortic valve holder to fully understand the benefits of the present invention. FIGS. 1 and 2 show an existing holder 20 of the prior art attached to the outflow end of a prosthetic aortic valve 22. There are many designs for prosthetic aortic valves in the art, the one shown being the Carpentier-Edwards PERIMOUNT (CEP) Pericardial Aortic Bioprosthesis from Edwards Lifesciences of Irvine, Calif., whose construction details are expressly incorporated by reference herein.

The aortic valve 22 comprises a peripheral fabric-covered stent structure 24 supporting a plurality, typically three, of flexible leaflets 26 that define the occluding surfaces of the valve. As mentioned, the holder 20 attaches to an outflow end of the valve 22 defined by a plurality of upstanding commissure posts 28. A sewing ring 30 defines the inflow end of the valve 22. The sewing ring 30 is used to attach the valve 22 to the aortic annulus, and may be circular and planar, or scalloped as shown. The sewing ring 30 defines a suture-permeable cuff made of an inner body of silicone covered with fabric.

As seen in the cutaway portion on the left of FIG. 2, the stent structure 24 comprises an inner stent 32 of semi-rigid material such as a biocompatible metal or polymer that is covered with fabric and to which the leaflets 26 are sewn, or otherwise attached. In the PERIMOUNT valve, tabs of adjacent leaflets 26 extend outward through an axial gap defined by the inner stent 32 and are wrapped around an insert (not shown) and secured in a bundle 34 to the outside of the inner stent. This particular construction has proven to reduce wear on the leaflets 26. After being covered with a further layer of fabric, the bundle 34 presents an outward bulge on the commissure posts 28, as seen on the right side of FIG. 2. It is important to understand that other flexible leaflet valve designs also have similar bulges or thicknesses at the commissure posts that define the outer extent of the posts.

It should be understood that the prior art holder 20, although possessing a track record of proven functionality, is somewhat more bulky than some surgeons find desirable. The holder 20 includes a central hub 40 defining a central axis. The hub 40 includes a central bore 42 that opens toward the outflow end (the holder orientation matches the valve orientation) and includes internal threads for receiving a delivery handle (not shown). Three relatively stubby legs 44a, 44b, 44c project radially outward from an inflow end of the central hub 40. As seen in the top view of FIG. 1, each of the legs 44 defines a width that is constant from the central hub 40 to an outer end 46. An exemplary width of the legs 44 is typically a constant 0.240 inches (6.1 mm), while the diameter of the circle circumscribed by the outer ends 46 of the legs differs for different sized valves. Prosthetic aortic valves are commonly provided in sizes between 19-31 mm in 2 mm increments, the size roughly representing the size of the annular orifice in which the valve will be implanted. The diameter of the valve 22 is thus somewhat larger because of its construction.

The diameter of the prior art holder 20 exceeds that of the commissure posts 28 as seen in FIGS. 1 and 2. For example, a 19 mm prosthetic aortic valve has an inner stent 32 with a nominal diameter at its inflow end of about 0.654 inches (16.6 mm). The holder 20 for the 19 mm valve has a diameter of 0.748 inches (19 mm). The inner stent 32 may be tapered slightly inward toward its outflow commissures, thus describing a conical shape. An exemplary taper is about 5°. However, even with the bulge created by the commissure post construction, the outer extent of the stent structure 24 at the commissure posts 28 is slightly less than the holder diameter, as seen in FIGS. 1 and 2. In another example, the inner stent 32 for a 31 mm valve has a nominal diameter of 1.16 inches (29.5 mm), while the holder 20 for that valve has a diameter of 1.22 inches (31 mm).

Attachment members such as sutures 48 pass through holes or openings provided in each of the legs 44 and extend downward (in the inflow direction) outside of each of the commissures 28 of the valve and loop through the sewing ring 30 (see FIG. 2). A groove or cavity 50 is typically provided on the outflow side of each of the legs 44 over which the attachment suture 48 crosses. The tautly-strung sutures 48 across the grooves 50 present an easy target for the surgeon to sever the sutures using a sharp and release the holder 20 from the valve 22. That is, the free ends of each suture 48 are tied to the holder 20, and severing a midpoint of each suture permits the now free strands to be pulled from the valve 22.

Again, it should be emphasized that the holder 20 depicted in FIGS. 1 and 2 is entirely functional, and has been in use for many years. The present invention is an improvement on the holder 20 primarily in that it is slimmer and increases visibility of the valve 22 below. As mentioned above, prosthetic aortic valves are introduced into the body leading with their inflow end and sewing ring 30. The holder 22 and attached handle are used to position the valve 22 with the sewing ring 30 against the annulus. Prior to finally tying off the attachments sutures, the handle is removed but the holder remains in place to help protect the valve from damage and because of the often flexible nature of flexible leaflet prosthetic valves. Only after the sewing ring 30 is completely secured will the holder 20 be removed.

The prior art holder 20 extends radially outward past the outer extent of the commissure posts 28 and thus somewhat occludes the surgeon's vision around the exterior of the valve 22 in the region of the commissure posts. This inhibits the surgeon's ability to parachute the valve through the sino-tubular junction, and inhibits visibility and maneuverability outside the commissure posts 28 during the annulus attachment phase. Furthermore, the legs 44 are relatively wide from the central hub 40 to their outer ends 46, which somewhat obscures the surgeon's view of the valve leaflets 26. Surgeons often wish to manually open the leaflets 26 to inspect the interior of the inflow side of the valve before tying down the implant sutures, and the bulk of the holder 20 gets in the way of this inspection.

In addition, the prior art technique of attaching the holder 20 to the valve 22, with the attachments sutures 48 extending outside of the commissures 28 and looping through the sewing ring 30, is somewhat undesirable. That is, some surgeons have experienced less than ideal tactile feedback by this attachment configuration because the connection between the holder 20 and the valve 22 is not very rigid. This can inhibit the surgeon's ability to verify that the valve has been correctly seated in the patient's annulus if the valve moves relative to the holder.

The present invention provides several embodiments of aortic valve holders that address the previous concerns. It should be emphasized that the three exemplary embodiments illustrated and described with respect to FIGS. 3-8 are representative of numerous configurations, and the invention is most accurately defined by the appended claims. The holders are shown attached to a prosthetic aortic valve 22 as previously described, and corresponding numbers will therefore be used.

Figure 3:
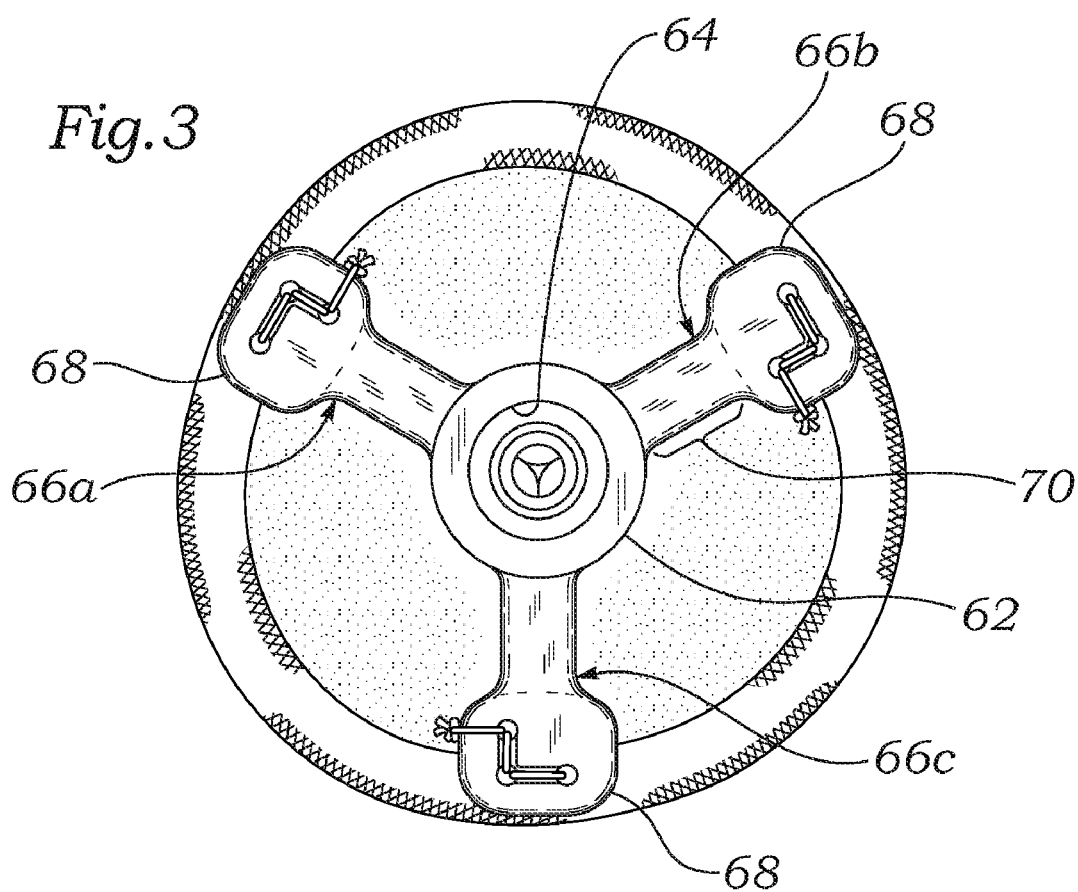
FIGS. 3 and 4 are top plan and front elevational views, respectively, of an exemplary holder of the present invention having a "dog bone" configuration attached to a flexible leaflet aortic valve.
Figure 4:
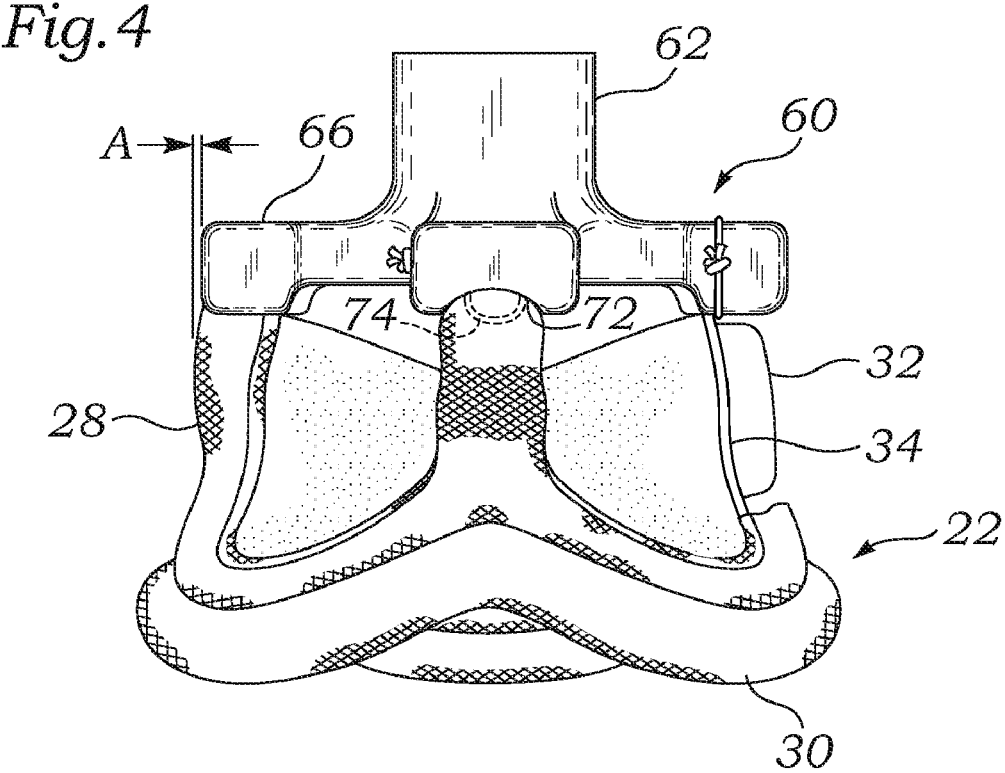

Looking at FIGS. 3 and 4, a first exemplary holder 60 again comprises a central hub 62 arranged about an axis and having a central bore 64 for receiving a delivery handle (not shown). Three legs 66a, 66b, 66c project outwardly from an inflow end of the central hub 62 and terminate in outer ends 68. As seen in the plan view of FIG. 3, each of the outer ends 68 has a first width that is quite a bit larger than the width of a mid-section 70 that extends between the outer end and the central hub 62.

In an exemplary embodiment, the mid-section 70 desirably is a single member having a width that is less than 50% of the width of the outer end 68, preferably 33% or less. Therefore, if each outer end 68 has a width in plan view of 0.240 inches (6.1 mm), the width of the mid-section 70 is desirably 0.120 inches (3.0 mm) or less, preferably 0.080 inches (2.0 mm) or less. The reduction in the width of the mid-section 70 results in a structure, in plan view, wherein each leg 66 resembles the end of a dog-bone. Providing a slimmer or narrower mid-section 70 of each leg 66 as illustrated greatly increases the visibility of the valve 22 during implantation. The outer ends 68 could likewise be slimmed such that the width of the entire structure is 0.120 inches (3.0 mm) or less, preferably 0.080 inches (2.0 mm) or less, though a certain width is desirable to provide enough material for the valve attachment structure, and the outer ends generally do not get in the surgeon's way.

To enhance the visibility and maneuverability around the exterior of the valve 22, the holder legs 66 are shortened relative to the prior art holder. As seen in FIG. 4, the legs 66 are reduced in radial dimension such that they project radially outward to contact the commissure tips at the radial location of the inner stent 32, but not as far as the outer radial extent of the commissure posts 28. The dimension A depicts this as measured between the outer radial extent of the legs 66 and the outer radial extent of the commissure posts 28. By retracting the legs 66 in this manner, visibility of the outer portions of the valve 22 at the location of the commissure posts 28 is greatly improved, thus facilitating advancement along the parachute sutures through the sino-tubular junction, as well as increasing the space around the valve for the surgeon to tie down the implant sutures.

As seen in FIG. 4, the holder legs 66 are further improved by providing a concave inflow surface 72 that matches the generally convex shape of the commissure post tips. This mating shape helps prevent relative movement between the holder 62 and valve 22. Moreover, the sutures attaching the holder 62 to the valve 22 no longer extend along the commissure posts to the sewing ring 30. Instead, each attachment suture 74 loops just through the commissure post tip, extending no farther toward the inflow end of the heart valve 22. By virtue of this direct connection between the outer ends 68 of the holder 62 and the tips of the commissure posts 28, as well as the concave configuration of the inflow surface 72, the connection between the holder 62 and valve 22 is greatly rigidified. This significantly improves the surgeon's control of advancement of the heart valve 22 into the target annulus by rendering the assembly much more rigid and supplying enhanced tactile feedback, much like stiffer shocks in a sports car.

It should be understood that the exclusive and direct connection between the outer ends 68 of the holder 62 and the tips of the commissure posts 28 is a significant advantage to all prior art holders. Most known holders are constructed to attach with sutures to the inflow sewing ring, as seen in FIG. 1. Some other holders provide attachments to the cusps of the valve as well as to the commissures. To the inventor's knowledge, there are no prior art holders that attach exclusively and directly to the commissure post tips on the outflow end of the valve, and in particular using attachments sutures that loop through the commissure post tips without extending to the sewing ring at the inflow end of the valve. The term, "attach exclusively and directly to the commissure post tips" means that the exclusive points of attachment are provided by attachment members (e.g., sutures) that extend from the holder just to the commissure tips. As mentioned above, this rigid combination of holder 62 and valve 22 will provide significant benefits to the surgeon during implantation of the valve. As with the prior art holders, the attachment sutures desirably cross over a cavity or groove provided in the outflow surface of the holder 62 and enable quick release by severing the sutures.

Although the attachment sutures 74 are the most common means for securing the valve to the holder, it is conceivable that clips, staples, clamps, or the like may also be used. In this regard, the term "attachment members" covers all these as well as equivalent alternatives.

Figure 5:
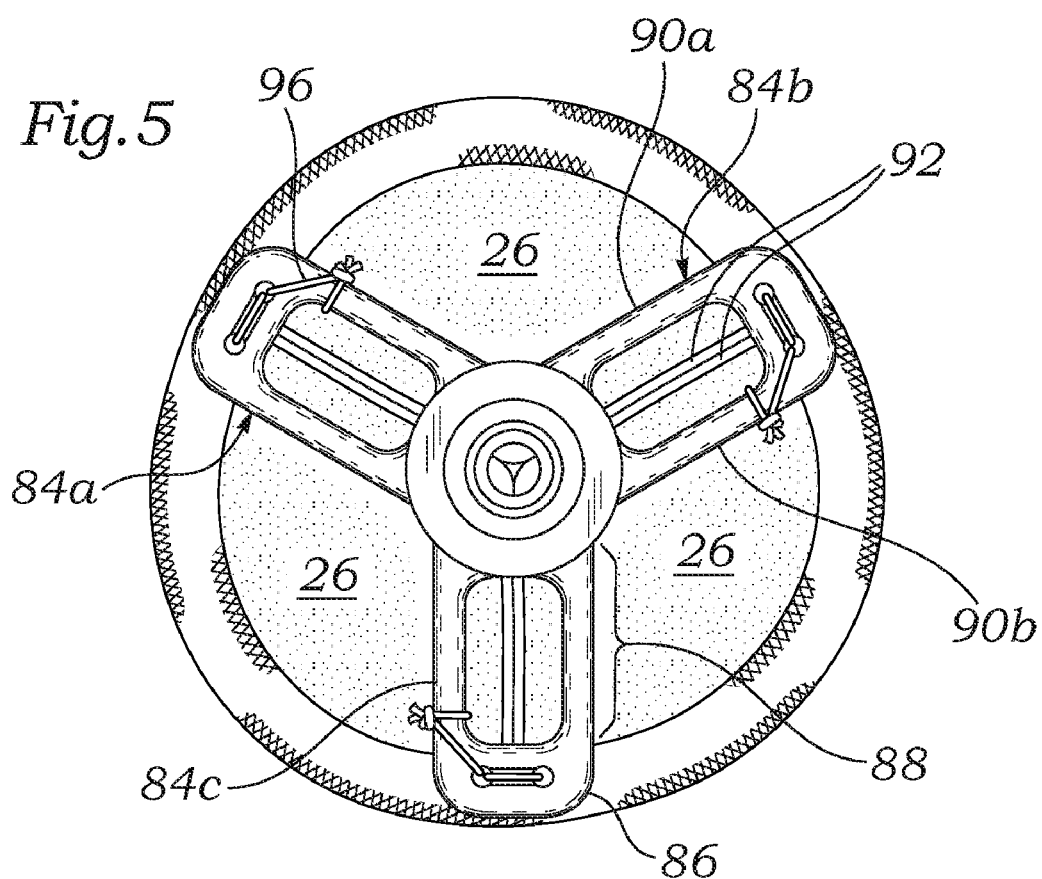
FIGS. 5 and 6 are top plan and front elevational views, respectively, of an exemplary holder of the present invention having a "split rail" configuration attached to a flexible leaflet aortic valve.
Figure 6:
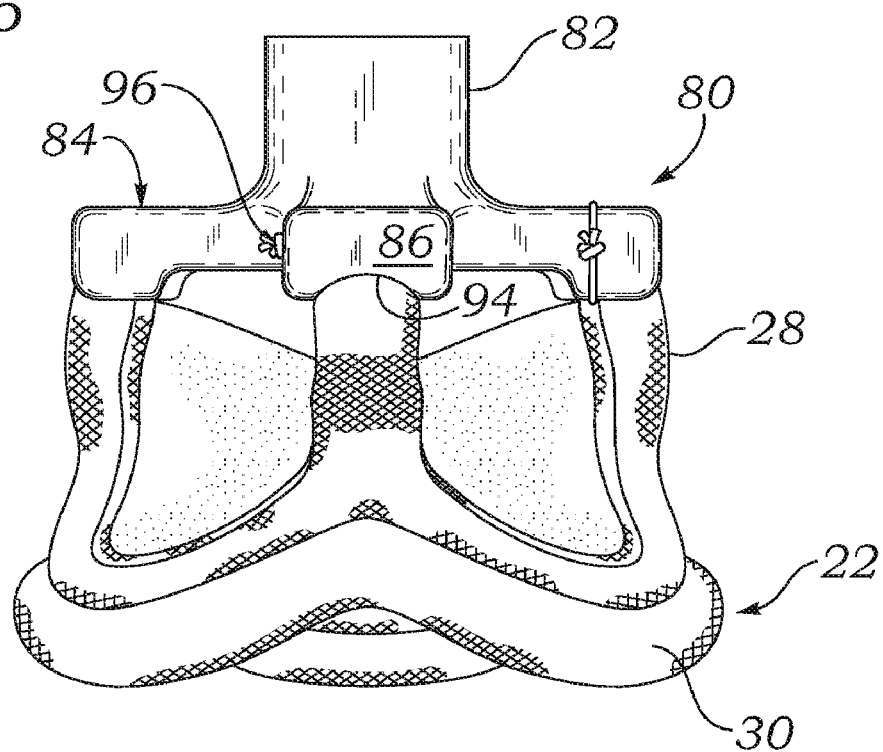

Now with reference to FIGS. 5 and 6, a second exemplary aortic valve holder 80 is shown attached to a prosthetic aortic valve 22. The holder 80 includes a central hub 82 having an outflow bore for receiving a handle (not shown), and three legs 84a, 84b, 84c terminating in outer ends 86. Each of the outer ends 86 connects to the central bore 82 along a mid-section 88 defined by two parallel rails 90a, 90b. The rails 90a, 90b converge at the outer ends 86, and a radial gap is formed therebetween enabling direct axial viewing of the heart valve therethrough. In particular, free edges 92 of the leaflets 26 are visible looking axially through the gap between the rails 90a, 90b. This feature enhances the surgeon's ability to open the leaflets 26 and inspect the interior inflow side of the valve 22 prior to tying down implant sutures.

As with the first exemplary holder 60, the legs 84 of the holder 80 have mid-sections 88 that possess less than 50% of the width of the outer ends 86, preferably 33% or less. Although the mid-sections 88 are split into the two rails 90a, 90b, the "total material width," and thus obstacle to viewing the valve, as seen in axial plan view is less than 50% of the width of the outer ends 86. For example, if the outer ends 86 have a width in plan view of 0.240 inches (6.1 mm), the total material width of the mid-sections 88, equaling the combined width of the two rails 90a, 90b, is desirably 0.120 inches (3.0 mm) or less, preferably 0.080 inches (2.0 mm) or less. In a particularly preferred embodiment, each of the rails 90a, 90b has a width in plan view of 0.030 inches (0.76 mm), for a total material width of 0.060 inches (1.5 mm), thus forming a gap therebetween of 0.18 inches (4.6 mm). In this example, the total material width of the mid-sections 88 is equal to 25% of the width of the outer ends 86. Again, the reduction in obstacles to visibility greatly enhances the task of the surgeon during implant.

The second exemplary holder 80 also shares certain other advantageous features with the first holder 60. First of all, the legs 84 are retracted in radial dimension such that they do not extend radially outward as far as the outer extent of the commissure posts 28 (as shown in FIG. 6). Furthermore, each of the legs 84 has a concave undersurface 94 at its outer end 86 that conforms to the generally convex profile of the tip of the corresponding commissure post 28. Finally, the attachment sutures 96 tied to the outer ends 86 pass only through the tips of the commissure posts 28, and do not connect to the inflow sewing ring 30.

A third exemplary holder 100 is shown in FIGS. 7 and 8 attached to the prosthetic aortic valve 22. The holder 100 includes a central hub 102 and three outwardly projecting legs 104a, 104b, 104c. As with the second embodiment, each of the legs 104 includes a mid-section 106 that is bifurcated into two rails 108a, 108b that converge at an outer end 110. The outer end 110 includes the attachment structure needed to secure valve attachment sutures 112.

In contrast to the second embodiment, each leg 104 is vaulted in the axial direction away from the outer ends 110, and thus the valve 22. That is, as seen in FIG. 8, the mid-section 106 of each leg 104 (i.e., each rail 108a, 108b) includes a segment 114 having an axial component that serves to raise the central hub 102 upward away from the valve 22 in comparison with the second holder 80 whose legs are generally radially directed.

In the illustrated embodiment, the mid-section 106 of each leg 104 has an inwardly and upwardly (radially and axially)

angled segment 114 as well as a purely radial segment 116. Of course, the same vaulted configuration could be created with legs 104 that were curved or simply angled in a straight line, and the illustrated embodiment should be considered exemplary only. The result is an axial component to each of the legs 104 that creates a larger axial space 120 directly beneath the holder 100 and between the holder and the prosthetic valve 22. This raised holder creates more visibility of the leaflet free edges 122 when viewed from the side. At the same time, the split rail design provides direct axial viewing of the leaflet free edges 122. In a preferred embodiment, the axial component of each of the legs 100 is desirably between 50-100% of the radial dimension of each of the legs 104.

The third exemplary holder 100 has the same desirable features as the first and second holders 60, 80. Namely, the legs 104 do not extend radially outward as far as the commissure posts 28 (as shown in FIG. 8), and each has a concave undersurface 124 at its outer end 110 that conforms to the generally convex profile of the tip of the corresponding commissure post 28. Finally, the outer ends 110 are secured directly and only to the tips of the commissure posts 28, preferably using sutures, and do not connect to the inflow sewing ring 30. Again, anchoring the holder 100 directly and exclusively to the tips of the commissure posts 28 supplies the surgeon with enhanced tactile feedback.

One other advantageous feature of any of the holder embodiments described herein is an improved connection between the central hub and the delivery handle (not shown). In the current design, the central hub has a simple internally threaded bore having six free running threads that mate with external threads on the distal end of the delivery handle. Some surgeons comment that this requires too many turns to screw in and unscrew the handle, and the running threads render the holder somewhat loose on the handle, thus permitting relative lateral movement between handle and holder. To solve this problem, the number of threads is desirably reduced to three, and a binding torque created that comes into play during the last full turn of the handle before it bottoms out. Alternatively, a snap-fit quick attachment feature can be provided as an alternative to the mating threads. Either of these solutions ensures a more secure engagement between the central hub and delivery handle so that the holder/handle connection does not become loose during suture placement through the sewing ring, and fewer handle revolutions are required to screw in and unscrew the handle from the holder, thus facilitating the implant process.

In a preferred embodiment, the holders 60, 80, 100 described herein are molded from polyoxymethylene (DELRIN). As seen in the drawings, the outer ends of the legs of the holders are chamfered or well-rounded to further enhance visibility and maneuverability around the holder. The holder has no moving parts that engage and manipulate the valve, unlike certain prior designs, thus minimizing costs. Moreover, the holder may be molded into a variety of elegant shapes as exemplified by the preceding embodiments.

Furthermore, the structural features of each of the embodiments described herein may be combined with any other feature. Therefore, for instance, the "vaulted" feature of the holder 100 could also be combined with the "dog-bone" holder 60 of FIGS. 3 and 4. Also, any one of the advantageous features described herein could be combined into the current holder 20 by itself. That is, for example, the current holder 20 could be attached to the prosthetic aortic valve by passing attachment sutures only through the tips of the commissure posts 28, as opposed to the sewing ring 30.

While the invention has been described in its preferred embodiments, it is to be understood that the words that have been used are words of description and not of limitation. Therefore, changes may be made within the appended claims without departing from the true scope of the invention.

What is claimed is:

1. A prosthetic heart valve holder comprising a central hub defining a central axis and a plurality of elongated legs projecting outwardly from an inflow end of the hub, each of the legs terminating at an outer end having valve attachment structure and a first width as seen in axial plan view, each of the legs further including an elongated single member mid-section extending between the central hub and the outer end, and each mid-section is narrower than the outer ends, wherein an inflow side of the outer end of each of the holder legs has a concave configuration.

2. The holder of claim 1, wherein each of the legs has an axial component so as to vault the central hub axially from the outer ends of the legs.

3. The holder of claim 2, wherein each of the legs has an axially and radially angled segment and a purely radial segment.

4. The holder of claim 1, wherein each holder leg includes a cavity on the outer end of the outflow side shaped to receive thereover an attachment suture to attach the holder to a prosthetic heart valve such that the suture may be easily severed using a sharp descending into the cavity.

5. The holder of claim 1, wherein the outer end of each leg has a first width as seen in axial plan view, and the elongated mid-section has a total material width as seen in axial plan view that is less than 50% of the first width for enhanced visibility of a valve secured to the holder.

6. The holder of claim 5, wherein the elongated mid-section has a total material width as seen in axial plan view that is less than 33% of the first width.

7. The holder of claim 1, wherein the outer end of each leg resembles the end of a dog-bone.

8. A prosthetic heart valve holder comprising a central hub defining a central axis and a plurality of elongated legs projecting outwardly from an inflow end of the hub, each of the legs terminating at an outer end having valve attachment structure and a first width as seen in axial plan view, each of the legs further including an elongated mid-section extending between the central hub and the outer end, and the elongated mid-section has a total material width as seen in axial plan view that is less than 50% of the first width for enhanced visibility of a valve secured to the holder.

9. The holder of claim 8, wherein the mid-section of each of the legs is split into two slim rails that are joined together at the outer end, and a radial gap is formed between the rails enabling direct axial viewing therethrough of a heart valve attached to the holder.

10. The holder of claim 9, wherein each of the two slim rails has an axial component so as to vault the central hub axially from the outer ends of the legs.

11. The holder of claim 9, wherein each of the two slim rails has an axially and radially angled segment and a purely radial segment.

12. The holder of claim 8, wherein an inflow side of the outer end of each of the holder legs has a concave configuration.

13. The holder of claim 8, wherein each holder leg includes a cavity on the outer end of the outflow side shaped to receive thereover an attachment suture to attach the holder to a prosthetic heart valve such that the suture may be easily severed using a sharp descending into the cavity.

14. The holder of claim 8, wherein the elongated mid-section has a total material width as seen in axial plan view that is less than 33% of the first width.

15. A prosthetic heart valve holder comprising a central hub defining a central axis and a plurality of elongated legs projecting outwardly from an inflow end of the hub, each of the legs terminating at an outer end having valve attachment structure and a first width as seen in axial plan view, each of the legs further including an elongated single member mid-section extending between the central hub and the outer end, and each elongated single member mid-section is narrower than the outer ends, wherein each holder leg includes a cavity on the outer end of the outflow side shaped to receive thereover an attachment suture to attach the holder to a prosthetic heart valve such that the suture may be easily severed using a sharp descending into the cavity.

16. The holder of claim 15, wherein each of the legs has an axial component so as to vault the central hub axially from the outer ends of the legs.

17. The holder of claim 16, wherein each of the legs has an axially and radially angled segment and a purely radial segment.

18. The holder of claim 15, wherein the outer end of each leg has a first width as seen in axial plan view, and the elongated mid-section has a total material width as seen in axial plan view that is less than 50% of the first width for enhanced visibility of a valve secured to the holder.

19. The holder of claim 18, wherein the elongated mid-section has a total material width as seen in axial plan view that is less than 33% of the first width.

20. The holder of claim 15, wherein the outer end of each leg resembles the end of a dog-bone.

21. A prosthetic heart valve holder comprising a central hub defining a central axis and a plurality of elongated legs projecting outwardly from an inflow end of the hub, each of the legs terminating at an outer end having valve attachment structure and a first width as seen in axial plan view, each of the legs further including an elongated single member mid-section extending between the central hub and the outer end, and the elongated single member mid-section has a total material width as seen in axial plan view that is less than 50% of the first width for enhanced visibility of a valve secured to the holder.

22. The holder of claim 21, wherein each of the legs has an axial component so as to vault the central hub axially from the outer ends of the legs.

23. The holder of claim 22, wherein each of the legs has an axially and radially angled segment and a purely radial segment.

24. The holder of claim 21, wherein the outer end of each leg resembles the end of a dog-bone.

25. A prosthetic heart valve holder comprising a central hub defining a central axis and a plurality of elongated legs projecting outwardly from an inflow end of the hub, each of the legs terminating at an outer end having valve attachment structure and a first width as seen in axial plan view, each of the legs further including an elongated single member mid-section extending between the central hub and the outer end, and each elongated single member mid-section is narrower than the outer ends, wherein the outer end of each leg resembles the end of a dog-bone.

26. The holder of claim 25, wherein each of the legs has an axial component so as to vault the central hub axially from the outer ends of the legs.

27. The holder of claim 26, wherein each of the legs has an axially and radially angled segment and a purely radial segment.

* * * * *